United States Patent [19]

Sano

[11] Patent Number: 5,214,454
[45] Date of Patent: May 25, 1993

[54] FUNDUS CAMERA

[75] Inventor: Eiichi Sano, Tokyo, Japan

[73] Assignee: Kabushiki Kaisha Topcon, Tokyo, Japan

[21] Appl. No.: 780,181

[22] Filed: Oct. 21, 1991

[30] Foreign Application Priority Data

Oct. 22, 1990 [JP] Japan .................................. 2-285152

[51] Int. Cl.⁵ ............................................. A61B 3/14
[52] U.S. Cl. .................................... 351/206; 351/205; 351/221
[58] Field of Search ............... 351/206, 205, 221, 211, 351/213; 354/62

[56] References Cited

U.S. PATENT DOCUMENTS 4,799,783  1/1989  Takahashi et al. .................. 351/206

Primary Examiner—Rodney B. Bovernick
Assistant Examiner—Hung Xuan Dang
Attorney, Agent, or Firm—Finnegan, Henderson, Farabow, Garrett & Dunner

[57] ABSTRACT

A fundus camera having an illuminating optical system is provided with illuminating diaphragms for non-fluorescent photography and fluorescent photography. The illuminating diaphragm for non-fluorescent photography and the illuminating diaphragms for fluorescent photography respectively have light transmitting regions of different surface areas.

10 Claims, 2 Drawing Sheets

FUNDUS CAMERA

BACKGROUND OF THE INVENTION

1. Field of the Invention

This invention concerns an improved fundus camera which can take photographs other than by fluorescence (black and white, or color), and by fluorescence.

2. Description of the Prior Art

A fundus camera is known in the art wherein, except when taking photographs other than by fluorescence (black and white or color), a subject may be given an intravenous injection of the fluorescent agent fluorescein. The fundus of the subject's eye is illuminated by light in the visible wavelength region so as to excite this fluorescent agent and a photograph is taken by the fluorescence of the fluorescent agent. In this type of fundus camera, a photograph may also be taken by giving the subject an injection of the fluorescent agent indocyanin green and illuminating the fundus by light in the infra-red region so as to excite the fluorescent agent.

In this type of fundus camera, an annular diaphragm is provided as a stop in the illuminating optical system, this annular diaphragm being disposed in a substantially conjugate position to the front portion of the eye undergoing examination, and the illuminating light is guided to the eye via the diaphragm. The illuminating light becomes ring-shaped in the vicinity of the pupil of the eye, and this ring-shaped illumination is guided to the fundus through the periphery of the pupil so as to illuminate the fundus. For the purpose of observing the eye, this illuminating light is visible light. The light reflected by the fundus is then guided to observation and photographic optical systems through the central region of the pupil. The photographer first selects the part of the fundus it is desired to photograph, and then selects an appropriate photographic mode. When exciting a fluorescent agent in order to photograph the fundus, an exciter filter which passes only light of specific wavelengths is inserted in the optical path of the illuminating light. Further, a barrier filter which essentially transmits only the fluorescence emitted by the fluorescent agent due to excitation by the illuminating light, is inserted in the optical path of the photographic optical system.

As only specific wavelengths in the illuminating light are used when taking photographs by exciting the fluorescent agent, higher light intensities have to be used than when taking photographs other than by fluorescence.

In this conventional fundus camera, however, the fundus of the eye under examination is illuminated by a ring-shaped illumination obtained using a single annular diaphragm. The amount of light passing through this diaphragm was insufficient, and consequently, good observations and photographs could not be obtained by fluorescence. Further, if the fundus were illuminated by infra-red light to excite the fluorescent agent, an even greater amount of light is required.

SUMMARY OF THE INVENTION

It is therefore an object of the present invention to provide a fundus camera wherein it is unnecessary to increase the light amount from the illuminating light source in order to make observations and take photographs by exciting a fluorescent agent, and wherein good photographs can still be obtained by fluorescence.

To achieve the above object, the present invention provides a fundus camera which can take both photographs other than by fluorescence and photographs by fluorescence, this camera comprising an annular diaphragm to vary the amount of light illuminating the fundus so as to be suitable either for taking photographs other than by fluorescence, or for taking photographs by fluorescence.

According to the fundus camera of the present invention, the amount of illuminating light can be varied according to the photographic mode selected, and so an illumination amount suitable for the chosen mode can be obtained even if the light amount from the light source does not increase above the necessary level when making observations or taking photographs by exciting a fluorescent agent.

BRIEF DESCRIPTION OF THE DRAWINGS

FIG. 1 is a drawing of the optical system of the camera.

DESCRIPTION OF THE PREFERRED EMBODIMENTS

Figure 1:
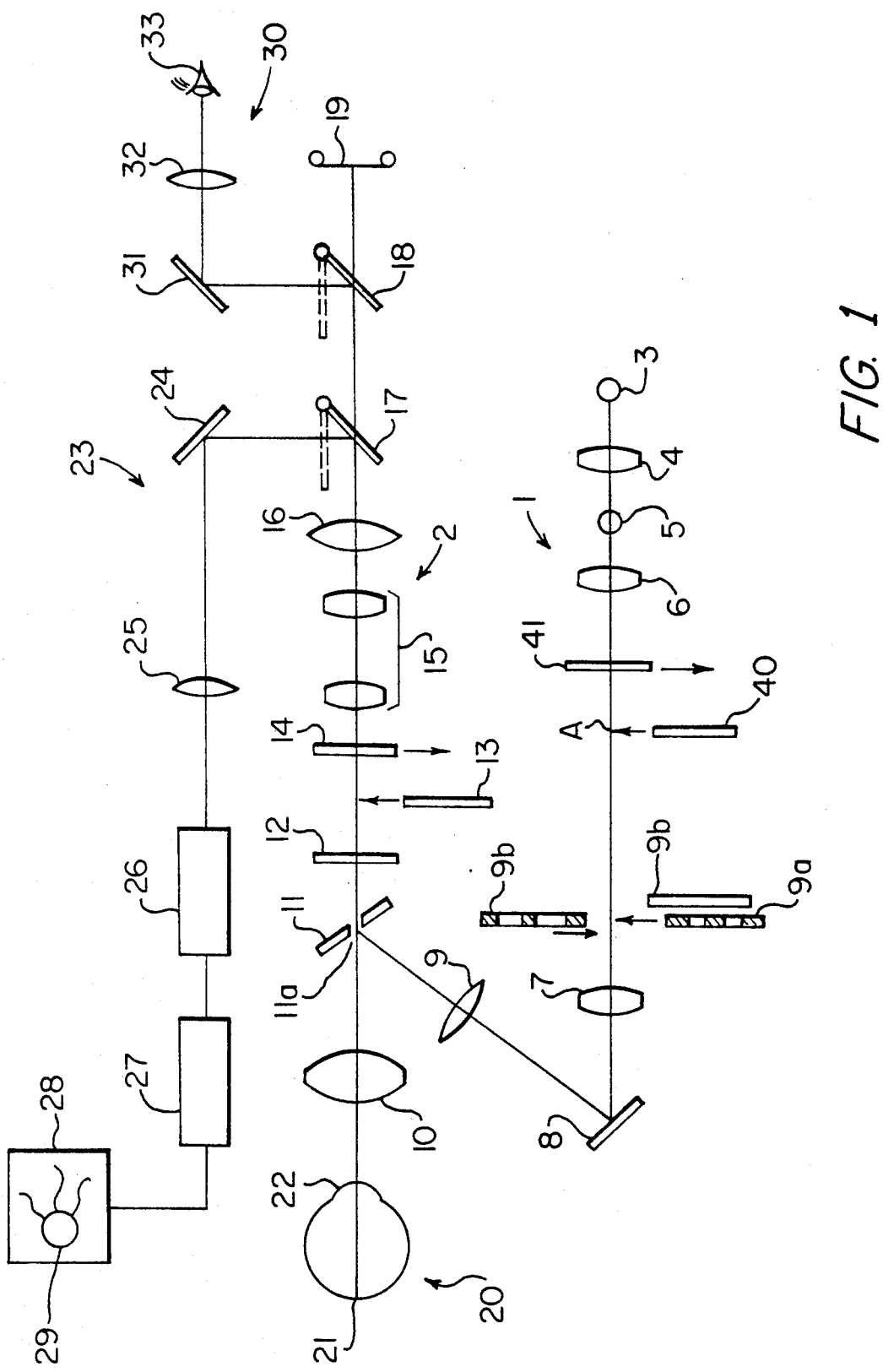
FIGS. 1 and 2 are drawings illustrating one embodiment of the fundus camera according to the present invention.
Figure 2A:
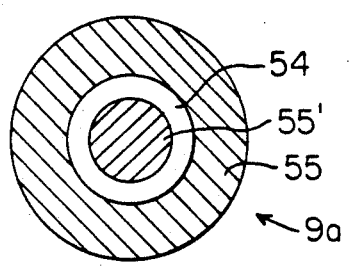
FIGS. 2(A), (B), (C) are schematic diagrams of an annular diaphragm.
Figure 2B:
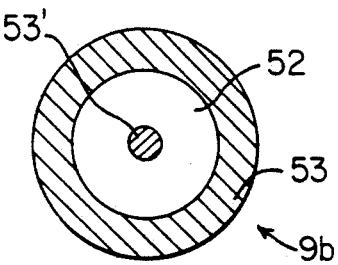
Figure 2C:
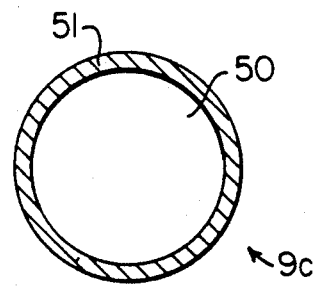

FIGS. 1 and 2 are drawings illustrating one embodiment of the fundus camera according to the present invention. In FIG. 1, 1 is an illuminating optical system and 2 is a photographing optical system. The illuminating optical system 1 basically comprises a halogen lamp 3 and a condensing lens 4 as an observational light source, and a xenon lamp 5, condensing lens 6, relay lens 7, total reflecting mirror 8 and relay lens 9 as a photographic light source. Exciter filters 40, 41 are inserted between the relay lens 7 and the condensing lens 6 for the purpose of fluorescent photography. The exciter filter 40 is used for the purpose of fluorescent photography under visible light illumination, while the exciter filter 41 is used for the purpose of fluorescent photography under infra-red illumination. As shown in FIGS. 2(A), (B), (C), one of three annular illuminating diaphragms 9a, 9b, 9c is inserted between the position A at which the exciter filter 40 is inserted and the relay lens 7. The illuminating diaphragm 9a comprises an annular transmitting part 54 and obstructing parts 55, 55'. The illuminating diaphragm 9b comprises an annular transmitting part 52 and obstructing parts 53, 53'. The illuminating diaphragm 9c comprises a circular transmitting part 50 and an obstructing part 51.

The illuminating diaphragm 9a is used for observation and photography under visible light illumination. Observations under visible light illumination are also performed in the case of fluorescent photography under visible light illumination, and fluorescent photography under infra-red illumination.

The illuminating diaphragm 9b is used for fluorescent photography under visible light illumination. The illuminating diaphragm 9c is used for fluorescent photography under infra-red illumination. These illuminating diaphragms 9a, 9b, 9c will be described hereinafter.

When taking fluorescent photographs under visible light illumination, the exciter filter 40 is inserted in the optical path between the condensing lens 6 and the relay lens 7 of the illuminating optical system 1, and when taking fluorescent photographs under infra-red illumination, the exciter filter 41 is inserted in the same position. FIG. 1 illustrates the situation with the exciter filter 41 inserted between the condensing lens 6 and the relay lens 7.

The illuminating diaphragm 9a is inserted in the optical path of the illuminating optical system 1 at the same moment that the exciter filters 40, 41 are withdrawn from same. The illuminating diaphragm 9b is inserted in the optical path of the illuminating optical system 1 at the same moment that the exciter filter 40 is inserted in same. The illuminating diaphragm 9c is inserted in the optical path of the illuminating optical system 1 at the same moment that the exciter filter 41 is inserted in same. The area of the transmitting part 52 of the annular illuminating diaphragm 9b is larger than the area of the transmitting part 54 of the annular illuminating diaphragm 9a. Further, the area of the transmitting part 50 of the annular illuminating diaphragm 9c is larger than the area of the transmitting part 52 of the annular illuminating diaphragm 9b, and the areas of the transmitting parts of the annular diaphragms 9a, 9b, 9c are set to correspond to the amount of the illuminating light.

These annular diaphragms 9a, 9b, 9c are installed in approximately conjugate positions to the pupil 22 of the eye 20 under examination with respect to the relay lens 7, relay lens $\theta$ and objective lens 10.

The photographing optical system 2 broadly consists of the objective lens 10, a mirror 11 having a hole therethrough a photographic aperture diaphragm 12, barrier filters 13, 14, a focusing lens 15, an imaging lens 16, a path selecting mirror 17, a quick return mirror 18 and a film 19.

The objective lens 10 is situated close to the eye 20 under examination.

The barrier filter 18 is inserted between the photographic aperture diaphragm 12 and focusing lens 15 of the photographic optical system 2 when taking photographs under visible light illumination. The barrier filter 14 is inserted between the photographic aperture diaphragm 12 and focusing lens 15 of the photographic optical system 2 when taking photographs under infra-red illumination. These barrier filters 13, 14 move in synchronism with the exciter filters 40, 41. FIG. 1 illustrates the situation with the barrier filter 14 inserted between the aperture diaphragm 12 and the focusing lens 15.

For black and white or color photography by visible light illumination, the exciter filters 40, 41 are withdrawn from the optical path of the illuminating optical system 1, and the barrier filters 13, 14 are withdrawn from the optical path of the photographic optical system 2.

When making observations, illuminating light from the halogen lamp 3 passes via the condensing lenses 4, 6, relay lens 7, full reflecting mirror 8, relay lens $\theta$, mirror 11 and objective lens 10 to the eye 20 under examination so as to illuminate the fundus 21 of the eye 20. This illuminating light becomes ring-shaped when it passes through the pupil 22 of the eye 20.

The light beam from the fundus 21 is guided to the mirror 11 via the objective lens 10, and then via a hole 11a through the holed mirror 11, the photographic aperture diaphragm 12, focusing lens 15 and imaging lens 16 to the path selecting mirror 17. When making recordings on film, the path selecting mirror 17 is removed from the path of the photographic optical system 2 as shown by the broken line in the figure. When recording images, on the other hand, the path selecting mirror 17 is inserted in the optical path of the photographic optical system 2. The path selecting mirror 17 forms part of a television image receiving system 23. The television image receiving system 23 comprises a mirror 24, relay lens 25 and a CCD camera 26. The photoelectrically converted output of the CCD camera 26 is input to a signal processing circuit 27, and based on this converted output, the signal processing circuit 27 outputs an image signal to a television monitor 28. Based on this image signal, the television monitor 28 may, for example, display an image of a fundus 29.

The quick return mirror 18 is inserted in the optical path of the photographic optical system 2 when making observations for the purpose of photography under visible light illumination. The light beam reflected from the fundus 21 is subsequently reflected by quick return mirror 18 and enters the eye 33 of an operator via a mirror 31 and eyepiece lens 32 of an eyepiece optical system 30.

This permits observation of the fundus 21 of the eye 20 under examination.

When taking color or black and white photographs under visible light illumination, the illuminating diaphragm 9a is inserted in the illuminating optical system, a xenon lamp 5 is switched on by a photographic switch, not shown, and a light amount suited to black and white or color photographs under visible light illumination illuminates the fundus 21. The light reflected from the fundus 21 is then guided to the film 19, and a good film recording is obtained.

When taking fluorescent photographs under visible light illumination, the subject is given an intravenous injection of fluorescein, and the fluorescent photographing mode is selected, and the photographic switch is operated. Then the exciter filter 40 and the illuminating diaphragm 9b is inserted into the optical path of the illumination optical system 1 after xenon lamp 5 is illuminated. As the illuminating diaphragm 9b is inserted in the optical path of the illuminating optical system 1, a light amount greater than the amount transmitted when the illuminating diaphragm 9a is inserted for fluorescent photography is guided to the fundus 21, and the fundus 21 is thereby illuminated by a light amount suited to fluorescent photography under visible light illumination.

When taking fluorescent photographs under infra-red light illumination, the subject is given an intravenous injection of indocyanin green, and the fluorescent photographing mode is selected, and the photographic switch is operated. Then the exciter filter 41 and the illuminating diaphragm 9c is inserted into the optical path of the illumination optical system after xenon 5 is drived. As the illuminating diaphragm 9c is inserted in the optical path of the illuminating optical system 1, a light amount greater than the amount transmitted when the illuminating diaphragm 9b is inserted for fluorescent photography is guided to the fundus 21, and the fundus 21 is illuminated by a light amount suited to fluorescent photography under infra-red illumination. A good infra-red image of the fundus is thereby formed by the CCD camera 26.

Figure 3:
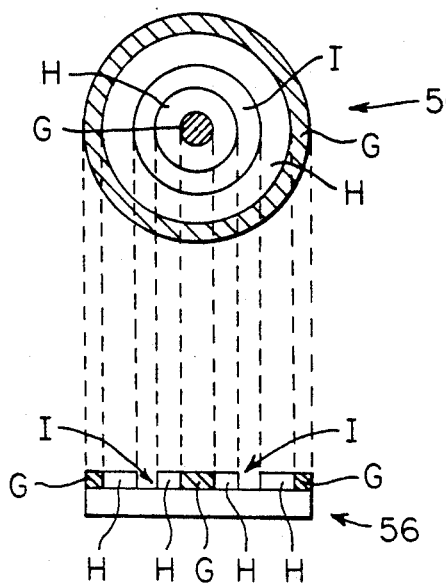
FIG. 3 is a drawing illustrating another embodiment of the fundus camera according to the present invention.

FIG. 3 shows a second embodiment of the fundus camera according to the present invention. 56 is a dichroic mirror having the property of transmitting only specific wavelengths of the illuminating light, and is in the form of a circular plate. The dichroic mirror 56 is fixed in the optical path of the illumination optical system. This dichroic mirror 56 has opaque regions G at the periphery and the center which block light of all wavelengths. Between the peripheral opaque region G and the central opaque region G, there is an annular area H which transmits mainly infra-red light of wavelength 750 nm, and effectively blocks all other wavelengths. Between the central opaque region G and the infra-red transmitting region H, there is also a region I which transmits light of all wavelengths. When the dichroic mirror 56 of the aforesaid construction is inserted between the filter for fluorescent photography under visible illumination at position A and the relay lens 7, the amount of illuminating light can be varied according to the photographic mode even if the illuminating diaphragms used for fluorescent photography are not inserted in the optical path of the illuminating optical system 1 in synchronism with the exciter filter used for same.

Figure 4A:
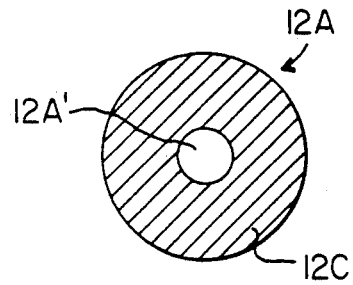
FIGS. 4(A) and (B) are schematic diagrams of the photographic aperture diaphragm.
Figure 4B:
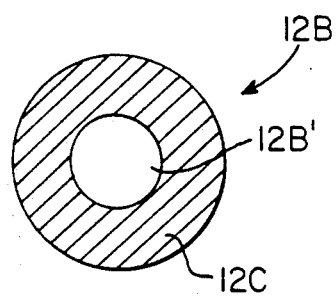

If, however there is insufficient light for taking photographs in any mode, the aperture of the photographic diaphragm 12 may be constructed in accordance with the structure of diaphragm 12A and a diaphragm 12B, shown in FIG. 4. The diaphragm 12B has a large aperture 12B' and the diaphragm 12A has a small aperture 12A'. The diaphragm 12A is inserted into the optical path of the photographic optical system 2 when color photographs are taken, the diaphragm 12B is inserted into the optical path of the photographic optical system 2 when fluorescent photographs are taken and the diaphragm 12A is withdrawn from the same. The area designated 12C is a nontransparent portion of diaphragms 12A and 12B.

Figure 5:
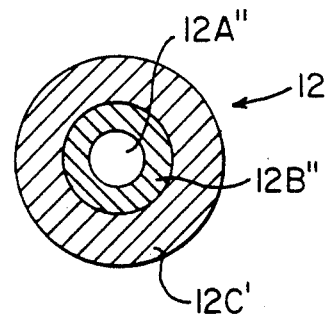
FIG. 5 is another schematic diagrams of the photographic aperture diaphragm.

FIG. 5 is another embodiment of the photographic aperture diaphragm 12. In FIG. 5, 12A" is an aperture, 12B" is a transparent portion of only infra-red light. 12C' is a nontransparent portion. This diaphragm 12 is fixed in the optical path of the photographic optical system 2.

What is claimed is:

1. An illuminating optical system, disposed along an optical axis for illuminating the fundus of an eye, in a camera for taking fluorescent and non-fluorescent photographs of the fundus of an eye, the illuminating optical system comprising:
   a light source disposed along said optical axis for emitting light in a range including at least visible light, infrared light and light of a desired excitation wavelength,
   a plurality of annular diaphragms capable of being inserted to or withdrawn from a position along said optical axis substantially conjugate with a pupil of the eye, including a first annular diaphragm for insertion to and withdrawal from said position when a fluorescent photograph is to be taken, said first annular diaphragm having a first cross-sectional area; and
   a second annular diaphragm for insertion to and withdrawal from said position when a non-fluorescent photograph, said second annular diaphragm having a second cross-sectional area different from said first cross-sectional area.

2. An illuminating optical system according to claim 1, wherein said second annular diaphragm is withdrawn from said position in synchronism with insertion of a filter for fluorescent photography along said optical axis, and said second annular diaphragm is inserted in said position in synchronism with withdrawal of said filter from along said optical axis.

3. An illuminating optical system according to claim 1, wherein said first annular diaphragm is inserted in said position in synchronism with insertion of a filter for fluorescent photography along said optical axis, and said first annular diaphragm is withdrawn from said position in synchronism with withdrawal of said filter from along said optical axis.

4. An illuminating optical system according to claims 1, 2, or 3 wherein an aperture diaphragm is provided along the optical axis for varying the light amount reflected from the fundus.

5. An illuminating optical system according to claims 1, 2, or 3 wherein fluorescent photography is carried out and said light source emits visible light.

6. An illuminating optical system according to any of claims 1, 2, or 3 wherein fluorescent photography is carried out and said light source emits infrared light.

7. An illuminating optical system according to claim 1 wherein said first cross-sectional area is larger than said second cross-sectional area.

8. An illuminating optical system, disposed along an optical axis for illuminating the fundus of an eye, in a camera for taking fluorescent and non-fluorescent photographs of the fundus of an eye, the illuminating optical system comprising:
   a light source disposed along said optical axis for emitting light in a range including at least visible light, infrared light and light of a desired excitation wavelength,
   an annular diaphragm disposed along said optical axis in a position substantially conjugate with a pupil of the eye comprising a circular stationary dichroic mirror including a first area capable of transmitting visible light and a second area capable of transmitting area infrared light, said first and second areas being different so as to vary the amount of illumination light dependent upon whether a fluorescent or non-fluorescent photograph is being taken.

9. A camera for taking fluorescent and non-fluorescent photographs of a fundus of an eye, comprising:
   illuminating optical means disposed along a first optical axis for illuminating the fundus of an eye, including
   a light source disposed along said first optical axis for emitting light in a range including at least visible light, infrared light and light of a desired excitation wavelength,
   a plurality of annular diaphragms capable of being inserted to or withdrawn from a position along said optical axis substantially conjugate with a pupil of the eye, including a first annular diaphragm for insertion to and withdrawal from said position when a fluorescent photograph is to be taken, said first annular diaphragm having a first cross-sectional area, and
   a second annular diaphragm for insertion to and withdrawn from said position when a non-fluorescent photograph is to be taken, said second annular diaphragm having a second cross-sectional area different from said first cross-sectional area; and photographing optical means for forming an image of the fundus the eye, including
- a projection means along a second optical axis for projecting light from the fundus onto a photographing plane,
- first barrier filter means capable of being placed into and out of said second optical axis for passing visible light, and
- second barrier filter means capable of being placed into and out of said second optical axis for passing infrared light.

10. A camera for taking fluorescent and non-fluorescent photographs of a fundus of an eye, comprising:
illuminating optical means disposed along a first optical axis for illuminating the fundus of an eye, including
- a light source disposed along said first optical axis for emitting light in a range including at least visible light, infrared light and light of a desired excitation wavelength, and
- an annular diaphragm disposed along said optical axis in a position substantially conjugate with a pupil of the eye comprising a circular stationary dichroic mirror including a first area capable of transmitting visible light and a second area capable of transmitting area infrared light, said first and second areas being different so as to vary the amount of illumination light dependent upon whether a fluorescent or non-fluorescent photograph is being taken; and photographing optical means for forming an image of the fundus the eye, including
- a projection means along a second optical axis for projecting light from the fundus onto a photographing plane,
- first barrier filter means capable of being placed into and out of said second optical axis for passing visible light, and
- second barrier filter means capable of being placed into and out of said second optical axis for passing infrared light.

* * * * *